(12) United States Patent
Bresina

(10) Patent No.: US 6,979,353 B2
(45) Date of Patent: Dec. 27, 2005

(54) APPARATUS FOR FUSING ADJACENT BONE STRUCTURES

(75) Inventor: Stephen Bresina, Davos Paltz (CH)

(73) Assignee: Howmedica Osteonics Corp., Mahwah, NJ (US)

( * ) Notice: Subject to any disclaimer, the term of this patent is extended or adjusted under 35 U.S.C. 154(b) by 111 days.

(21) Appl. No.: 10/004,969

(22) Filed: Dec. 3, 2001

(65) Prior Publication Data

US 2003/0105527 A1 Jun. 5, 2003

(51) Int. Cl.[7] ................................................. A61F 2/44
(52) U.S. Cl. ................................. 623/17.16; 623/17.11
(58) Field of Search ......................... 623/17.11, 17.12, 623/17.13, 17.14, 17.15, 17.16; 606/61

(56) References Cited

U.S. PATENT DOCUMENTS

| | | |
|---|---|---|
| 3,848,601 A | 11/1974 | Ma et al. |
| 4,743,256 A | 5/1988 | Brantigan |
| 4,834,757 A | 5/1989 | Brantigan |
| 4,878,915 A | 11/1989 | Brantigan |
| 5,192,327 A | 3/1993 | Brantigan |
| 5,425,772 A | 6/1995 | Brantigan |
| 5,429,863 A | 7/1995 | McMillin |
| 5,443,514 A | 8/1995 | Steffee |
| 5,458,638 A | 10/1995 | Kuslich et al. |
| 5,514,180 A * | 5/1996 | Heggeness et al. ...... 623/17.16 |
| 5,522,899 A | 6/1996 | Michelson |
| 5,554,191 A | 9/1996 | Lahille et al. |
| 5,607,424 A | 3/1997 | Tropiano |
| 5,609,635 A | 3/1997 | Michelson |
| 5,609,636 A | 3/1997 | Kohrs et al. |
| 5,645,596 A | 7/1997 | Kim et al. |
| 5,653,762 A | 8/1997 | Pisharodi |
| 5,658,336 A | 8/1997 | Pisharodi |
| 5,658,337 A | 8/1997 | Kohrs et al. |
| 5,669,909 A | 9/1997 | Zdeblick et al. |
| 5,683,463 A | 11/1997 | Godefroy et al. |
| 5,716,415 A | 2/1998 | Steffee |
| 5,749,916 A | 5/1998 | Richelsoph |
| 5,766,252 A | 6/1998 | Henry et al. |
| 5,776,199 A | 7/1998 | Michelson |

(Continued)

FOREIGN PATENT DOCUMENTS

| | | |
|---|---|---|
| EP | 0 880 950 A | 12/1998 |
| FR | 2 813 519 A | 3/2002 |
| WO | WO 02/17823 A | 3/2002 |

*Primary Examiner*—Pedro Philogene
(74) *Attorney, Agent, or Firm*—Lerner, David, Littenberg, Krumholz & Mentlik, LLP

(57) ABSTRACT

An apparatus for facilitating fusion of adjacent vertebrae includes an implant body dimensioned for positioning within an intervertebral space between upper and lower vertebrae to maintain the vertebrae in desired spaced relation to facilitate fusion thereof. The implant body includes lower and upper surfaces for engaging the respective lower and upper vertebrae and first and second side wall portions extending between the upper and lower surfaces. The first and second side wall portions are substantially solid. At least one of the first and second side wall portions have a substantially narrow longitudinal slit defined therein arranged to enhance flexibility of the one side wall portion. Preferably, each of the first and second side wall portions includes a longitudinal slit. The implant body may define an internal chamber dimensioned for reception of bone growth inducing substances. The implant body includes an internal bore extending through the upper and lower surfaces for reception of bone growth inducing substances. Preferably, the internal bore is cylindrical shaped to receive a cylindrical bone dowel harvested during the surgical procedure, or alternatively, to receive a prepackaged cylindrical rod containing bone growth inducing substances. A plurality of internal bores may be provided in side by side relation.

24 Claims, 9 Drawing Sheets

U.S. PATENT DOCUMENTS

| | | |
|---|---|---|
| 5,865,848 A | 2/1999 | Baker |
| 5,879,385 A | 3/1999 | Crockard et al. |
| 5,888,222 A | 3/1999 | Coates et al. |
| 6,039,762 A | 3/2000 | McKay .................... 623/17.11 |
| 6,113,638 A * | 9/2000 | Williams et al. ............ 128/898 |
| 6,123,705 A | 9/2000 | Michelson |
| 6,136,031 A | 10/2000 | Middleton ............... 623/17.16 |
| 6,241,771 B1 | 6/2001 | Gresser et al. |
| 6,245,108 B1 * | 6/2001 | Biscup .................... 623/17.11 |
| 6,315,797 B1 | 11/2001 | Middleton ............... 623/17.16 |
| 6,325,827 B1 | 12/2001 | Lin ........................ 623/17.16 |
| 6,371,987 B1 * | 4/2002 | Weiland et al. .......... 623/17.11 |
| 6,395,035 B2 * | 5/2002 | Bresina et al. ........... 623/17.15 |
| 6,629,998 B1 * | 10/2003 | Lin ........................ 623/17.11 |

\* cited by examiner

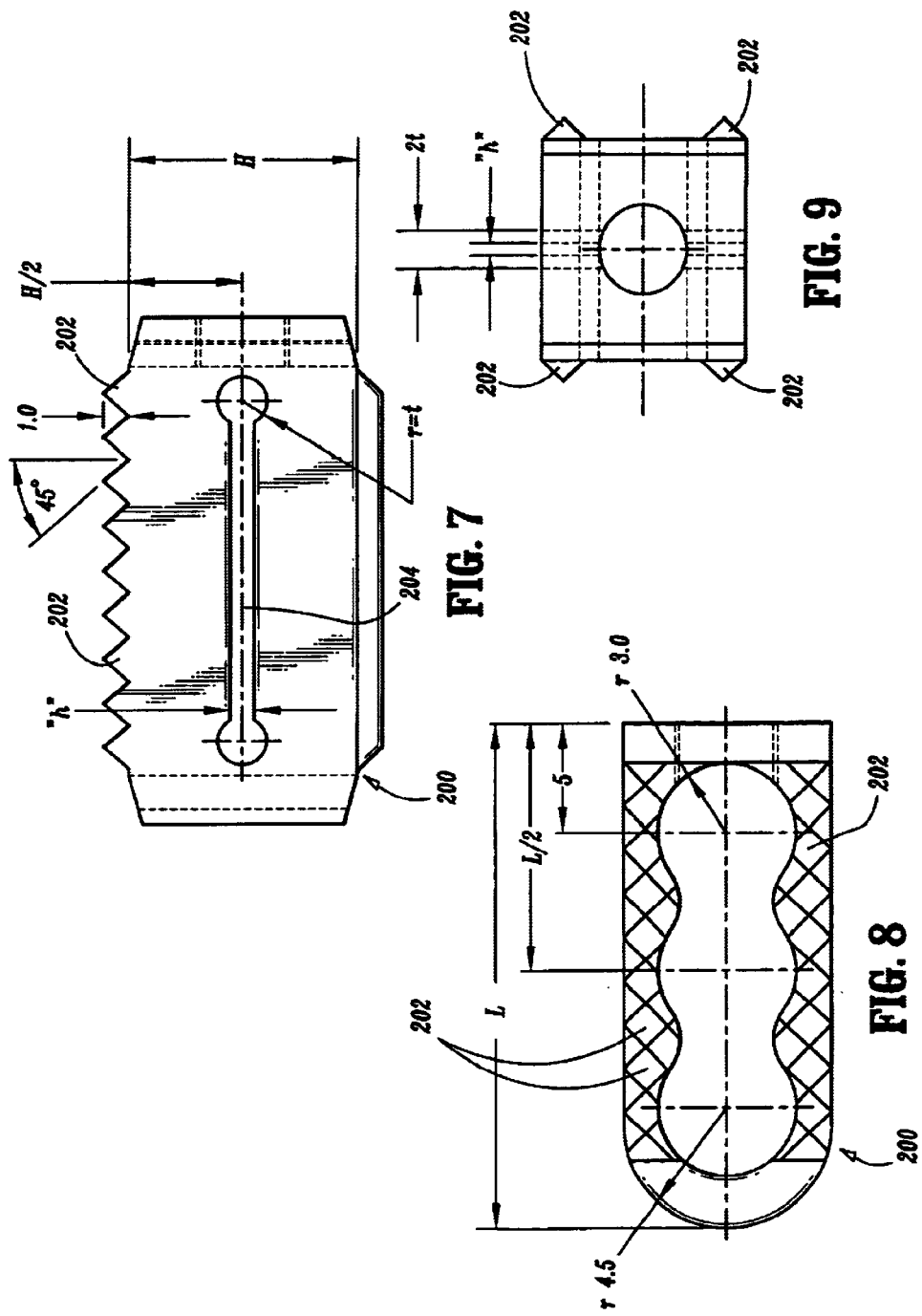

APPARATUS FOR FUSING ADJACENT BONE STRUCTURES

BACKGROUND

1. Technical Field

The present disclosure generally relates to fusion of adjacent bone structures, and, more particularly, to an apparatus and associated methods for fusing adjacent vertebrae.

2. Background of the Related Art

The fusion of adjacent bone structures is commonly performed to compensate for degenerative or deteriorated disorders in bone. For example, an intervertebral disc, which is a ligamentous cushion disposed between adjacent vertebrae, may undergo deterioration as a result of injury, disease, tumor or other disorders. The disk shrinks or flattens leading to mechanical instability and painful disc translocations.

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. More recently, emphasis has been placed on fusing bone structures (i.e., adjacent vertebrae) with metallic or ceramic implants. One fusion cage implant is disclosed in commonly assigned U.S. Pat. No. 5,026,373 to Ray et al. The Ray '373 fusion cage includes a cylindrical cage body having a thread formed as part of its external surface and apertures extending through its wall which communicate with an internal cavity of the cage body. The fusion cage is inserted within a tapped bore or channel formed in the intervertebral space thereby stabilizing the vertebrae and maintaining a pre-defined intervertebral space. If desired, a pair of fusion cages are implanted within the intervertebral space. The adjacent vertebral bone structures communicate through the apertures and with bone growth inducing substances which are within the internal cavity to unite and eventually form a solid fusion of the adjacent vertebrae. FIGS. 1–2 illustrate the insertion of a pair of the Ray '373 fusion cages positioned within an intervertebral space.

SUMMARY OF THE INVENTION

The present invention is directed to improved spinal fusion devices and procedures. In accordance with a preferred embodiment, an apparatus for facilitating fusion of adjacent vertebrae includes an implant body dimensioned for positioning within an intervertebral space between upper and lower vertebrae to maintain the vertebrae in desired spaced relation to facilitate fusion thereof. The implant body includes lower and upper surfaces for engaging the respective lower and upper vertebrae, and first and second side wall portions extending between the upper and lower surfaces. The first and second side wall portions are substantially solid. At least one of the first and second side wall portions has a substantially narrow longitudinal slit defined therein arranged to provide vertical flexibility of the one side wall portion thereby enabling dynamic support between adjacent vertebrae which, under certain conditions, enhances fusion. Preferably, each of the first and second side wall portions includes a longitudinal slit. The implant body may define an internal chamber dimensioned for reception of bone growth inducing substances. The internal chamber may be an internal bore extending through the upper and lower surfaces. Preferably, the internal bore is cylindrical shaped to receive a cylindrical bone dowel harvested during the surgical procedure or, alternatively, to receive a prepackaged cylindrical rod containing bone growth inducing substances. A plurality of internal bores may be provided in side by side relation.

The upper and lower surfaces of the implant body may include a plurality of ridges dimensioned to engage the respective upper and lower vertebrae to facilitate retention within the intervertebral space. Alternatively, the upper and lower surfaces of the implant body may include a plurality of grooves defined therein dimensioned to engage the respective upper and lower vertebrae.

The implant body further includes leading and trailing end portions. Preferably, at least one of the leading and trailing end portions has a tapered surface. In a desired embodiment, the implant body includes upper and lower tapered surfaces at each of the leading and trailing ends to ensure that the load carried by the implant body is focused on the more flexible central section of the implant body.

A method for facilitating fusion of adjacent vertebrae with the implant apparatus is also disclosed.

BRIEF DESCRIPTION OF THE DRAWINGS

Preferred embodiment(s) of the present disclosure are described herein with reference to the drawings wherein:

FIGS. 7–9 are side, top and axial views, respectively, of an alternate embodiment of an implant apparatus according to the present invention;

DETAILED DESCRIPTION OF PREFERRED EMBODIMENTS

A preferred embodiment of the apparatus and method disclosed herein are discussed in terms of orthopedic spinal fusion procedures and instrumentation. It is envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of a fusion implant utilized in performing a spinal fusion followed by a description of the preferred method for spinal fusion in accordance with the present disclosure.

In the discussion which follows, the term "proximal", as is traditional, will refer to the portion of the structure which is closer to the operator while the term "distal" will refer to the portion which is further from the operator.

Figure 3B:
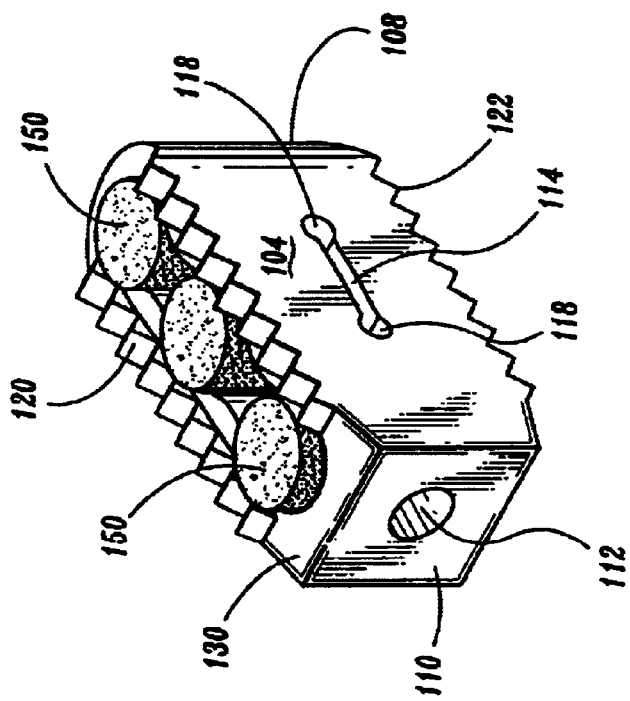
FIGS. 3A and 3B are perspective views of a first embodiment of a fusion implant apparatus in accordance with the principles of the present disclosure.
Figure 3A:
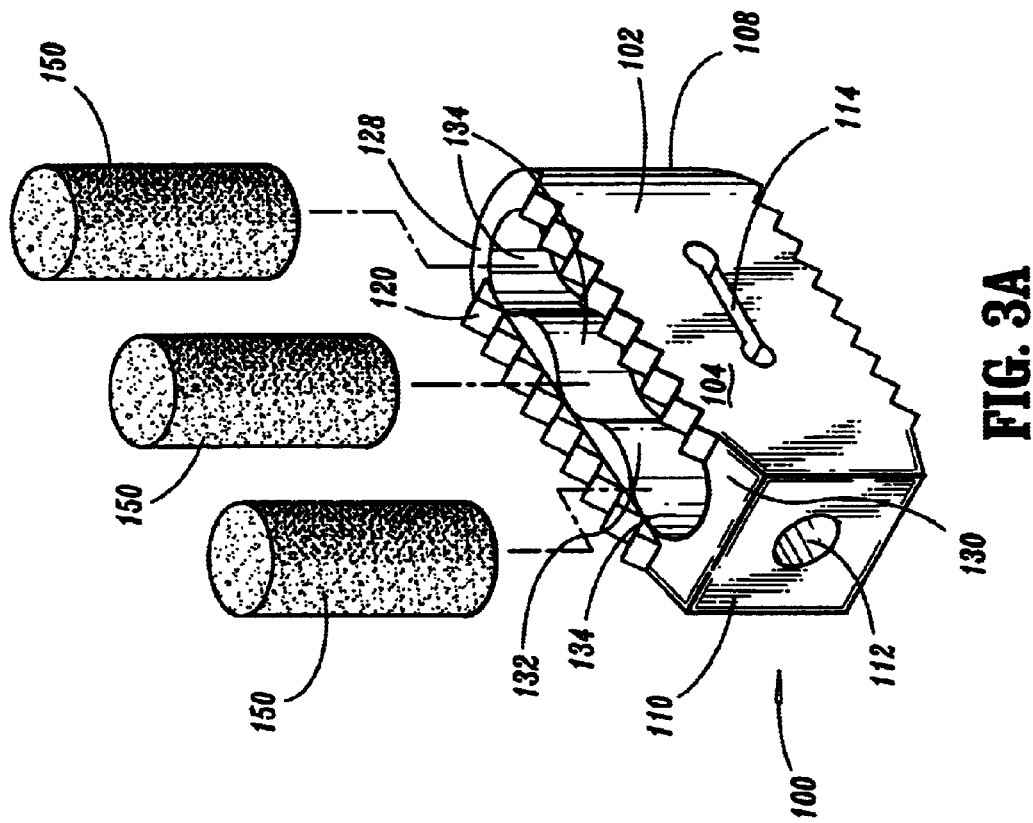

Referring now to the drawings in which like reference numerals identify similar or identical elements throughout the several views, FIGS. 3A and 3B illustrate in perspective, the fusion implant apparatus of the present disclosure. Fusion implant 100 is intended to be inserted within a preformed bore in adjacent bone structures, e.g., adjacent vertebrae, with the bore spanning the intervertebral space and penetrating the vertebral end plates. Fusion implant 100 is particularly intended for use in a posterior approach for spinal fusion; however, it is envisioned that other surgical approaches may be utilized including e.g., anterior, anterior-lateral, posterior-lateral, etc. Implant 100 is particularly intended for use in the lumbar of the vertebral column although the implant may have application in the cervical, thoracic areas as well.

Fusion implant 100 is preferably fabricated from a carbon reinforced PEKEKK (poly-ether-ketone-ether-ketone-ketone) material manufactured under the trade name, OstaPEK™, by Co-Ligne. PEKEKK is radiolucent and thus does not interfere with radiation procedures or obstruct viewing of surrounding tissues and structures. Alternatively, implant 100 may be made from PEEK (poly-ether-ether-ketone). In addition, implant 100 may be alternately fabricated from titanium and/or alloys of titanium, stainless steel, ceramic materials or rigid polymeric materials. Implant 100 is preferably sufficient in strength to at least partially replace the supporting function of an intervertebral disc, i.e., to maintain adjacent vertebrae in desired spaced relation, during healing and fusion.

Figure 2:
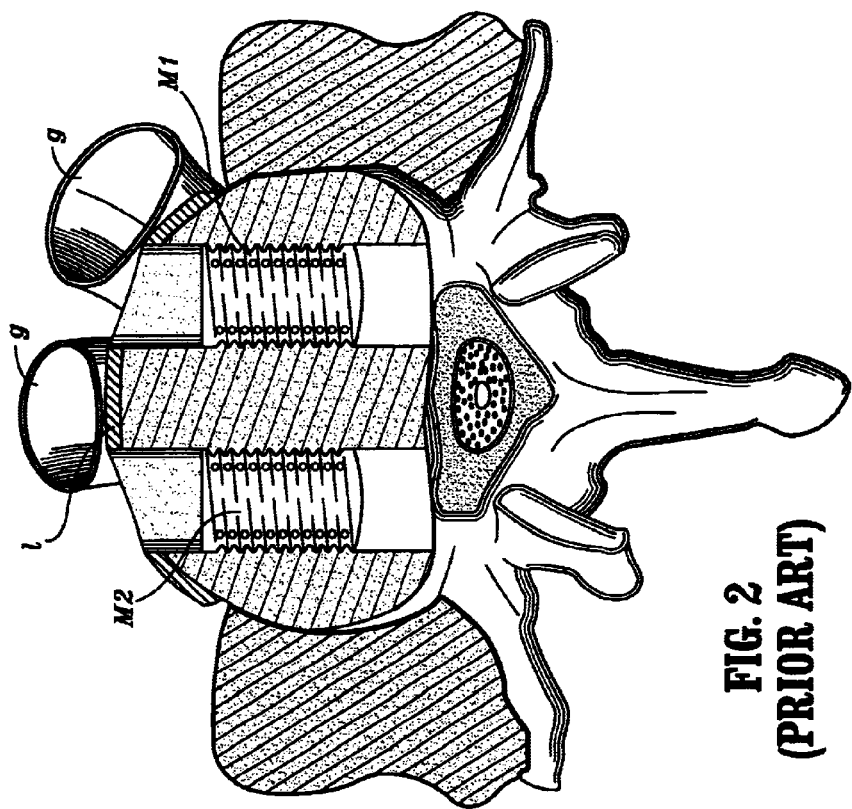
FIG. 2 is a view taken along line 2—2 of FIG. 1 illustrating a pair of prior art fusion implants positioned within the intervertebral space for fusion of adjacent vertebrae.
Figure 1:
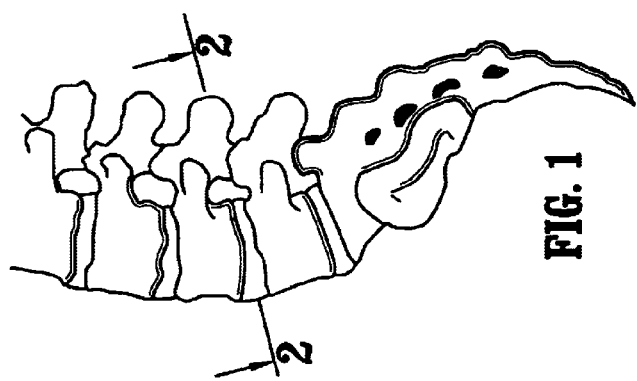
FIG. 1 is a view illustrating a portion of the vertebral column of a patient.
Figure 4:
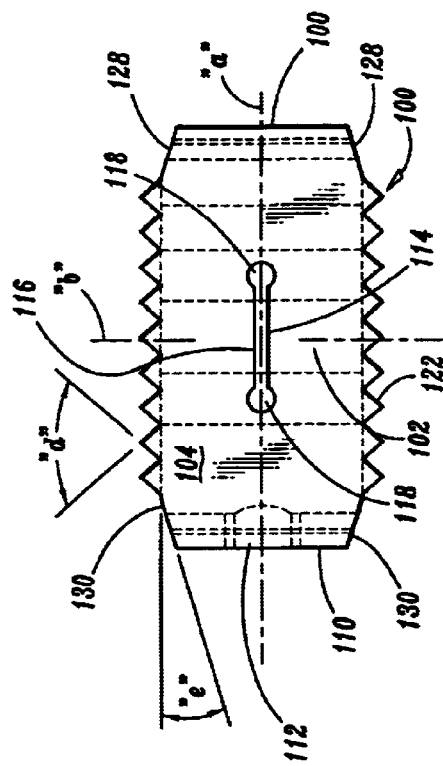
FIG. 4 is a side plan view of the first embodiment implant apparatus.
Figure 6:
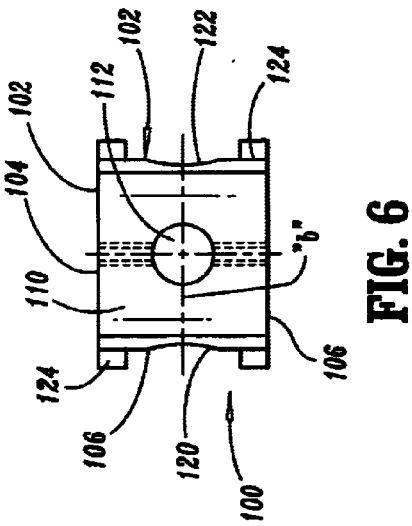
FIG. 6 is an axial view of the first embodiment implant apparatus.
Figure 3:
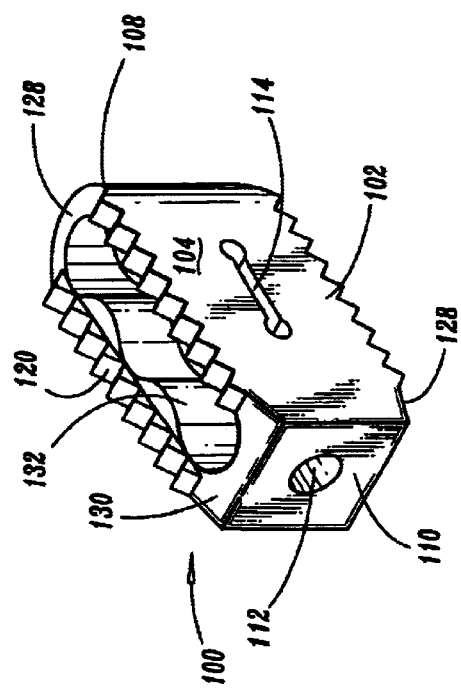
FIG. 3 is a perspective view of a first embodiment of a fusion implant apparatus in accordance with the present invention.
Figure 5:
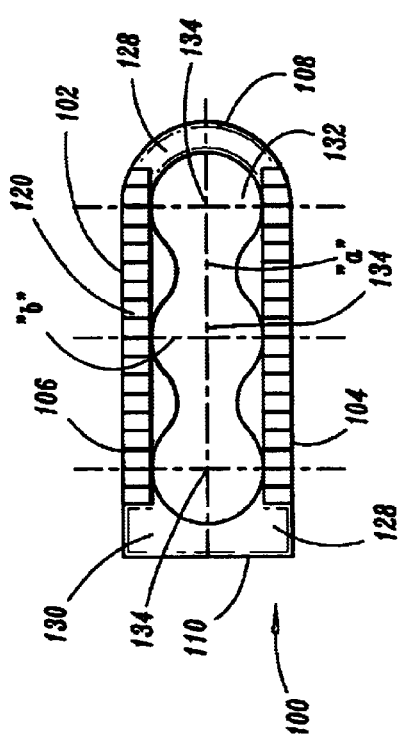
FIG. 5 is a top plan view of the first embodiment implant apparatus.

With reference now to FIGS. 4–6, in conjunction with FIGS. 3A and 3B, fusion implant 100 includes implant body 102 defining first or longitudinal axis "a" and second axis "b" which is transverse to the first axis "a". Implant body 102 includes first and second opposed planar side walls 104, 106, which extend in general parallel relation to each other and to first axis "a". Implant body 102 further includes leading or entry end wall 108 and trailing end wall 110. Entry end wall 108 is rounded defining a constant radius of curvature to facilitate entry of implant body 102 into the preformed bore. Trailing end wall 110 is generally planar and has an internal threaded bore 112 which receives the threaded end of an insertion tool to facilitate insertion of the implant within the preformed bore.

First and second side walls 104, 106 each include a single relatively narrow longitudinal slit 114 extending completely through the side wall. Each slit 114 is defined by a longitudinal section 116 and an arcuate or circular section 118 at each end of the longitudinal section 116. Longitudinal slit 114 extends for about ⅓ the overall length of the implant 100. Longitudinal slit 114 provides a degree of elasticity to implant body 102, particularly, the central section of the body 102, to subject the bone graft within the implant body 102 to a portion of the load exerted on the vertebral bodies. This facilitates the fusion process as will be discussed in greater detail hereinbelow. In addition, the narrow configuration of longitudinal slit 114 reduces invasion of interdiscal tissues and fluids into the interior of implant body 102 and facilitates retention of the graft within the implant body 102.

Implant body 102 further defines upper and lower surfaces 120, 122 which respectively engage the upper and lower vertebral portions upon insertion of the implant body 102 within the preformed bore. Upper and lower surfaces 120, 122 each includes a single row of ridges 124 projecting outwardly relative to implant body 102. Ridges 124 are generally pyramidal in shape having a pointed end 126 defining an angle "d" of about 90E (FIG. 4). Ridges 124 engage the vertebral bone tissue thereby minimizing the potential of retropulsion of implant body 102 from the intervertebral space to retain the implant body 102 within the vertebral bodies.

Upper and lower surfaces 120, 122 each include tapered surfaces 128,130 adjacent the leading and trailing ends 108, 110 of implant body 102. Tapered surfaces 128, 130 are arranged at an angle "e" ranging from about 10–20E, preferably about 15E relative to the longitudinal axis "a" of implant body 102. Tapered surfaces 128,130 ensure that the load carried by implant body 102 is concentrated at the more flexible central section of implant body 102, i.e., the section containing longitudinal slit 114. More specifically, tapered surfaces 128,130 are dimensioned to have minimal contact with the vertebral bone. In the absence of tapered surfaces 126,128, the leading and trailing solid ends 108, 110 of implant body 102 would carry the majority of the load and thus determine the stiffness of the cage. Consequently, this high concentration of the load at the leading and trailing ends 108, 110, would cause the bone graft to resorb locally and increase the potential for implant 100 to sink into the end plate.

Implant body 102 further includes an internal cavity 132 which extends through upper and lower surfaces 120, 122 of the implant body 102. Internal cavity 132 accommodates bone growth inducing substances such as bone graft, bone morphogenic protein (BMP), bone growth factors, etc. which facilitate the fusion process. Internal cavity 132 is preferably defined by a plurality of cylindrical bores 134 (e.g., three) arranged in side by side relation; however, more or fewer than three bores 132 may be provided. As best depicted in FIGS. 3A and 3B, the cylindrical shape of bores 134 preferably corresponds to the shape of a bone graft plug 150 harvested from the patient. In this manner, the cylindrical bone graft plug 150 can be easily introduced within implant body 102. Alternatively, the bone graft plug 150 can be substituted with prepackaged manufactured rods of bone graft substitute materials including allograft, autograft, bone morphogenic proteins (BMP), bioceramics and hydroxyapatite. The rods preferably define a circular cross-section and length corresponding in diameter and height to the cylindrical bores 134 of implant body 102. FIG. 3A illustrates the implant body 102 in an exploded view with the bone plugs or bone substitute rods 150 removed from bores 134. FIG. 3B depicts implant body 102 with bone graft plugs or bone substitute rods 150 positioned within cylindrical bores 134 of implant body 102. Thus, implant body 102 and plug or rods 150 form a kit for spinal fusion. The kit may incorporate two, three or more bone plugs or bone substitute rods with each plug or rod custom fitted to the cylindrical bore 134 of the implant body 102.

FIGS. 7–9 depict an alternate embodiment of fusion implant 100. In accordance with this embodiment, implant 200 includes multiple rows of ridges 202 (e.g., formed by knurling) to provide additional retention characteristics. In addition, longitudinal slit 204 extends along a major portion of the length of implant body 206 and defines a height "h" which is greater than the height of the slit of the prior embodiment. Such dimensioning of longitudinal slit 204 provides enhanced flexibility and elasticity which may be desirable depending on the surgical application.

Figure 11:
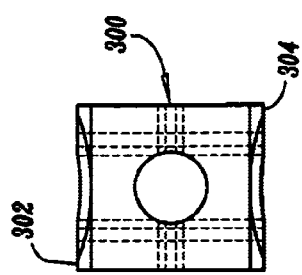
FIGS. 10–12 are side, axial and top views, respectively, of another late alternate embodiment of an implant apparatus according to the present invention.
Figure 10:
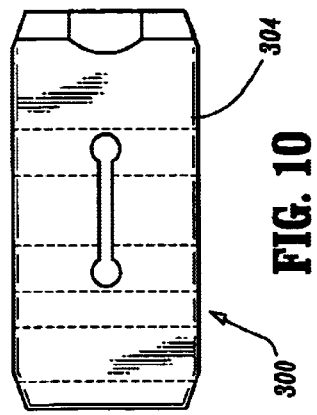
Figure 12:
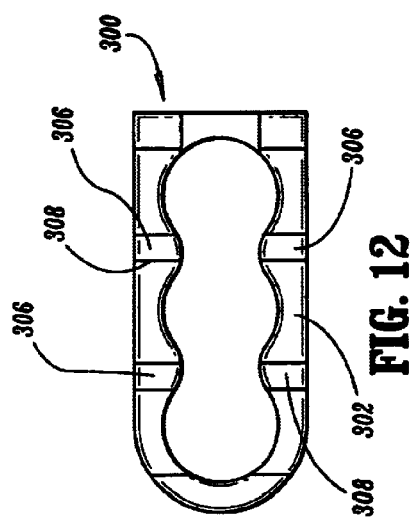

FIGS. 10–12 illustrates another alternative embodiment of the implant of the present invention. Implant 300 is substantially similar to implant 100 of FIGS. 3–6, but, includes upper and lower surfaces 302, 304 with transverse grooves 306. Grooves 306 define edges or surfaces 308 which engage the vertebral bone tissue to retain implant body 102 within the preformed bore.

Figure 13:
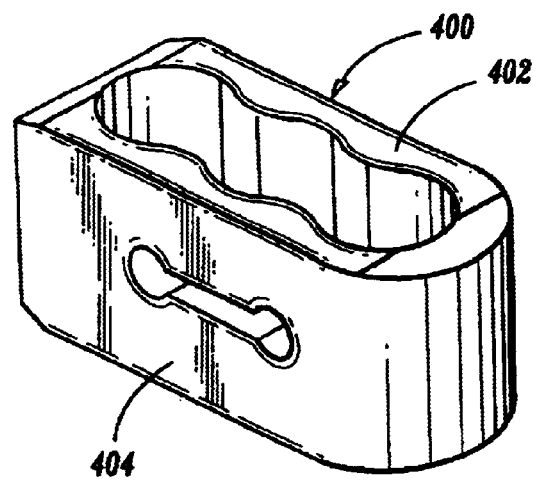
FIGS. 13–14 are frontal and r ear perspective views of another alternate embodiment of an implant apparatus according to the present invention.
Figure 14:
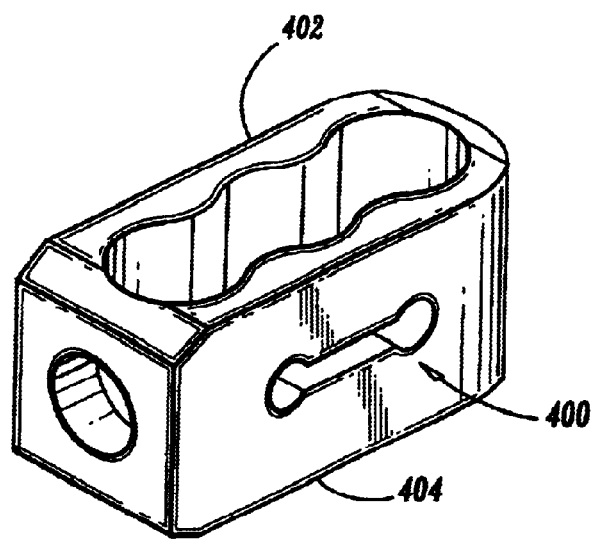
Figure 17:
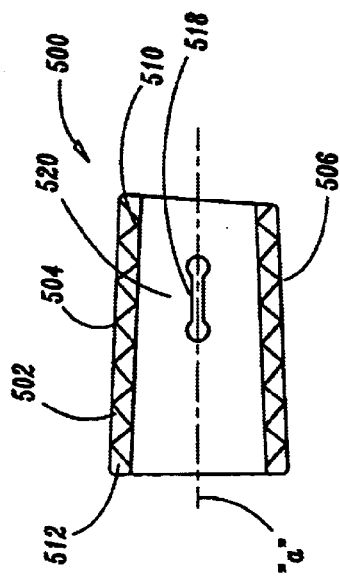
FIGS. 17–19 are side, top and axial views respectively of the implant of FIG. 16.
Figure 19:
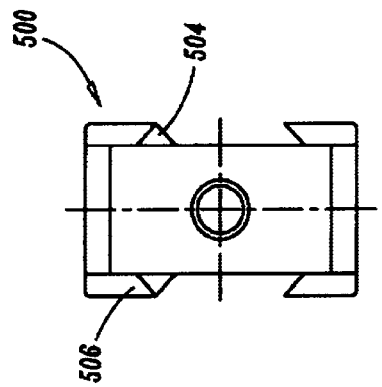
Figure 16:
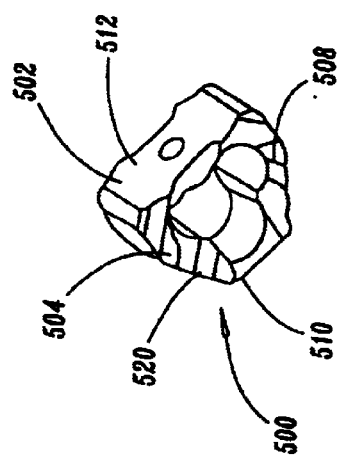
FIG. 16 is a perspective view of another alternate embodiment of an implant apparatus according to the present invention.
Figure 18:
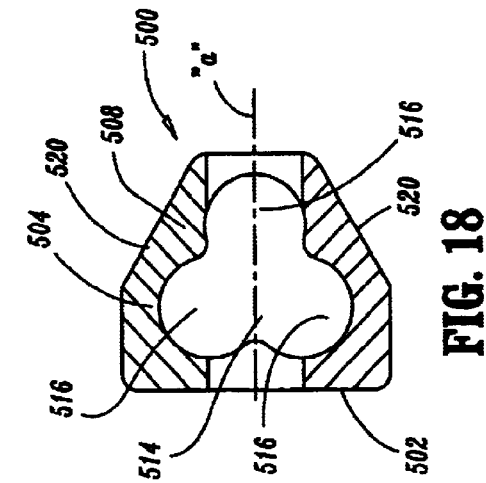

FIGS. 13–14 depict another alternate embodiment of the present invention. Implant 400 is substantially similar to the embodiment of FIGS. 3–6. Implant 400 is, however, devoid of ridges, or grooves, etc. in its lower and upper surfaces 402, 404. Upper and lower surfaces 402, 404 are substantially smooth as shown. Alternatively, it is envisioned that lower and upper surfaces 402, 404 may be coated with a suitable bone adhesive such as polymethyl methacrylate to facilitate retention relative to the vertebral bone.

FIGS. 16–19 illustrate yet another embodiment of the present invention. Implant 500 is particularly contemplated for an anterior approach for spinal fusion. Implant 500 includes implant body 502 defining a generally triangular shape with respect to the top view of FIG. 18. Implant body 502 includes upper and lower surfaces 504,506 with a plurality of ridges 508 extending obliquely with respect to the longitudinal axis "a" of implant body 502. Implant body 502 is wedge shaped having a leading end 510 defining a height "h" which gradually tapers outwardly toward the trailing end 512 of implant body 502. Implant body 502 has an internal cavity 514 defined by a clustered arrangement of cylindrical bores 516 extending through the upper and lower surfaces 504, 506 of implant body 502. Bores 516 receive cylindrical bone dowels or rods of prepackaged bone growth inducing substances as discussed hereinabove. Implant body 502 further includes longitudinal slots 518 (FIG. 17) disposed in forward wall surfaces 520 of implant body 502. Longitudinal slots 518 are similar in configuration and function to the slots of the aforedescribed embodiments. Trailing wall surfaces 522 of implant body 502 are devoid of longitudinal slots 518 to ensure that the flexibility of implant body 502 is dictated by the forward section of the implant body 502.

The implants of the aforedescribed embodiments may have various lengths ranging from about 18 mm–24 mm and corresponding various heights ranging from about 14 mm–18 mm. Other dimensions are also contemplated and may vary depending on the intended use of the implant in the cervical, thoracic or lumbar regions of the spine.

Insertion of Fusion Implant

The insertion of the fusion implant of the present disclosure into an intervertebral space defined between adjacent lumbar vertebrae will now be described. The subsequent description will be particularly discussed in conjunction with an open posterior approach for spinal fusion implant insertion of the implant 100 of FIGS. 3–6. However, it is to be appreciated that other approaches, e.g., anterior, lateral, posterior lateral, anterior lateral etc., could be utilized. Laparoscopic approaches may also be employed.

Figure 20:
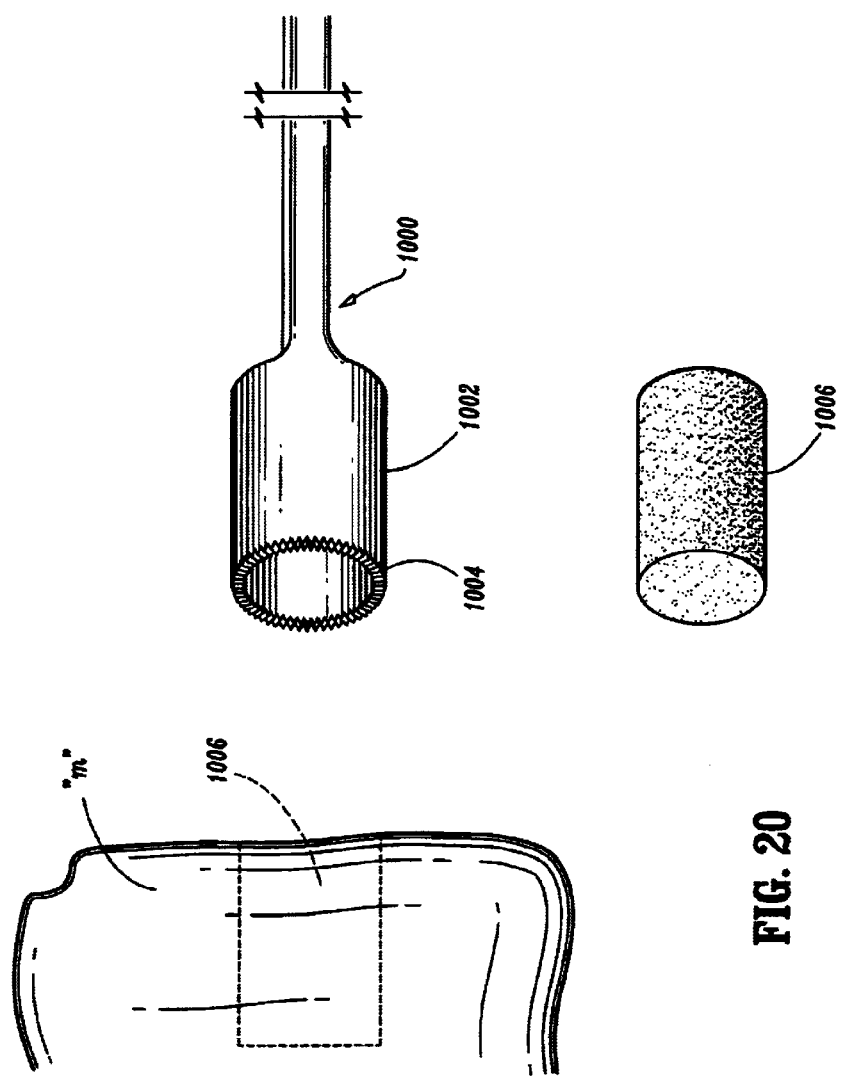
FIG. 20 is a view illustrating a surgical trephine used in preparing a cylindrical bone graft for positioning within an implant apparatus according to the present invention.

FIG. 20 illustrates a surgical trephine and cylindrical bone graft formed thereby which are used in conjunction with the preferred method of implantation of the implant apparatus 100. Trephine 1000 includes hollow drill portion 1002 having cutting teeth 1004. Drill portion 1002 is advanced into, e.g., the illiac crest "m" to core out a cylindrical bone dowel or graft 150 as depicted in FIG. 20. As indicated hereinabove in connection with the discussion of FIGS. 3A and 3B, this graft 150 preferably corresponds in dimension to a cylindrical bore 134 of implant body 102 for placement therein. Alternatively, the bone graft 150 may be substituted with prepacked cylindrical rods fabricated from bone growth inducing substances including the type discussed herein above.

Figure 21:
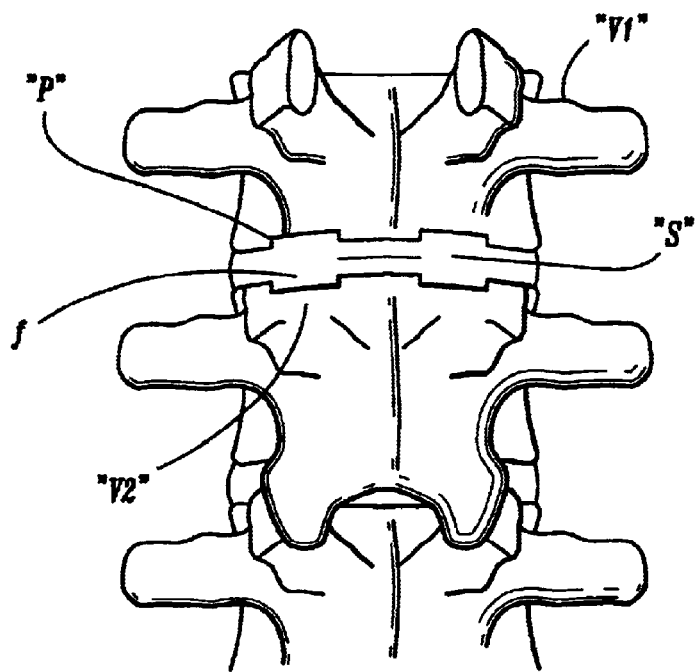
FIG. 21 is a view illustrating the vertebral column with implant receiving channels therein.

With reference now to FIG. 21 the surgical procedure is continued by accessing the intervertebral space "i" utilizing appropriate retractors, reamers, etc . . . to expose the posterior vertebral surface. A first bore "f" is prepared on one lateral side of the intervertebral space to penetrate the vertebral end plates "p" with appropriate instrumentation including rongeurs, osteotomes, rasps, or other suitable instruments. Thereafter, a second bore "s" is formed at the other lateral side.

Figure 22:
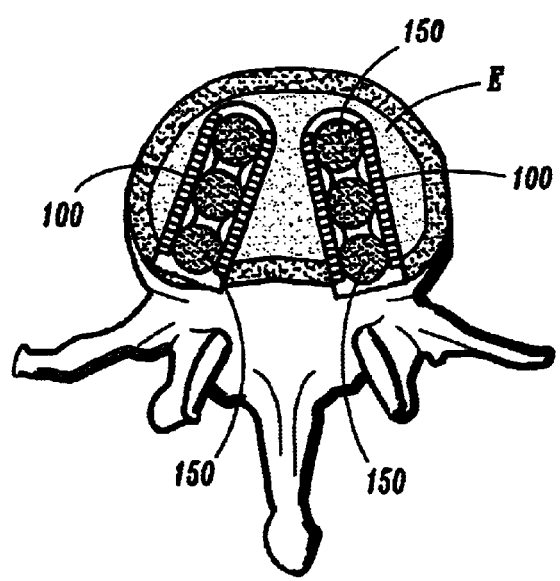
FIG. 22 illustrates a pair of implant apparatus according to the present invention with bone graft positioned within the implant receiving channels.

Preferably, each bore "f", "s" spans the intervertebral space "i" and penetrates the end plates "p" of the adjacent vertebral bone tissue "v1,v2". Implant 100 may then be packed with the bone graft. Once the graft(s) are obtained, they are positioned within respective cylindrical bores 134 of implant body 102. With reference now to FIG. 22, an implant 100 is positioned within each preformed bore within the adjacent vertebrae, preferably, advanced in the direction of axis "a" of the implant. The fusion implant 100 may be mounted on an insertion instrument (not shown) and advanced within the intervertebral space. Once implanted, implant body 102 and the bone graft or bone substitute rod 150 share the load exerted by the vertebral column as facilitated through the elasticity of the implant body 102 provided by the longitudinal slits 114. By allowing implant body 102 to share the load with the graft material, the graft has a significantly increased potential of forming bone and fusing the vertebral bodies.

Implants 100 form struts across the intervertebral space "i" to maintain the adjacent vertebrae "$V_1$, $V_2$" in appropriate spaced relation during the fusion process. Over a period of time, the adjacent vertebral tissue communicates with the bone graft plugs or rods 150 within bores 134 to form a solid fusion. Lateral vertebral tissue growth into the implant 100 is restricted due to the narrow configuration of longitudinal slit 114.

While the preferred embodiments have been disclosed, it is understood that alternate embodiments including modifications or changes may be made without departing from the scope of the present invention. For example, the fusion implant 100 could also be used for thoracic and cervical vertebrae.

What is claimed is:

1. An apparatus for facilitating fusion of adjacent vertebrae, comprising:
an implant body dimensioned for positioning within an intervertebral space between upper and lower vertebrae to maintain the vertebrae in desired spaced relation to facilitate fusion thereof, said implant body including lower and upper surfaces for engaging the respective lower and upper vertebrae, and first and second side wall portions extending between said upper and lower surfaces, said first and second side wall portions being substantially solid, at least one of said first and second side wall portions having a substantially narrow longitudinal slit defined therein arranged to enhance flexibility of said one side wall portion wherein said implant body includes two or more bores extending through said upper and lower surfaces for reception of bone growth inducing substances, said bores having intersecting wall portions forming a communication path extending from said upper to said lower surface, said bores in communication with said slit.

2. The apparatus according to claim 1 wherein each of said first and second side wall portions includes said longitudinal slit.

3. The apparatus according to claim 1 wherein said two or more bores of said implant body are generally cylindrically-shaped bores.

4. The apparatus according to claim 3 wherein said generally cylindrically-shaped internal bores are arranged in adjacent side by side relation and have open sides forming the communication path to adjacent bores.

5. The apparatus according to claim 1 wherein said upper and lower surfaces include a plurality of ridges, said ridges dimensioned to engage the respective upper and lower vertebrae to facilitate retention within the intervertebral space.

6. The apparatus according to claim 1 wherein said upper and lower surfaces include a plurality of grooves defined therein, said grooves defining surfaces dimensioned to engage the respective upper and lower vertebrae to facilitate retention within the intervertebral space.

7. The apparatus according to claim 1 wherein said implant body includes leading and trailing end portions, at least one of said leading and trailing end portions having a tapered surface.

8. The apparatus according to claim 7 wherein said one of said leading and trailing end portions includes upper and lower tapered surfaces.

9. The apparats according to claim 8 wherein each said leading and trailing end portions include said upper and lower tapered surfaces.

10. The apparatus according to claim 3 further including a bone growth inducing substance disposed within said cylindrically-shaped bore, said bone growth inducing substance defining a substantially cylindrically-shape corresponding to said cylindrically-shaped internal, bore of said implant body.

11. A method for fusion of adjacent vertebrae, comprising the steps of:
  accessing the intervertebral space defined between adjacent vertebrae;
  providing an implant including an implant body having lower and upper surfaces and first and second side wall portions extending between said upper and lower surfaces, said first and second side wall portions being substantially solid, at least one of said first and second side wall portions having a substantially narrow longitudinal slit defined therein arranged to enhance flexibility of said one side wall portion, said implant having an internal cavity formed by at least two bores extending between the upper and lower surface in communication with said slit said bores having side walls in continuous communication between said upper and lower surfaces; and
  positioning said implant within the intervertebral space whereby said upper and lower surfaces engage upper and lower vertebral portions of adjacent vertebrae in supporting relation therewith while said longitudinal slit permits compressive movement of said implant body in response to a load exerted by the vertebral portions.

12. The method according to claim 11 further including the step of introducing bone growth inducing substances within said at least two bores to facilitate fusion whereby said implant body and said bone growth inducing substances share the load exerted by the vertebral portions.

13. The method according to claim 12 wherein said implant body defines at least two generally cylindrically-shaped bores extending through said upper and lower surfaces and further including the step of harvesting a substantially cylindrically-shaped bone graft for positioning within said bore.

14. The method according to claim 13 wherein the step of harvesting includes using a trephine to harvest the bone graft.

15. The apparatus as set forth in claim 3 wherein there are three internal bores further including a generally cylindrical bone substitute plug within each of said generally cylindrical internal bores.

16. The apparatus as set forth in claim 15 wherein the cylindrical internal bores are arranged in adjacent side by side relationship.

17. A kit for fusion of adjacent vertebra comprising:
  a plurality of implants, each having an implant body including upper and lower surfaces for engaging respective adjacent vertebra and sidewall positions extending between said upper and lower surfaces and surrounding an internal cavity having a plurality of generally cylindrical internal bores open to said upper and lower surfaces, said bores having sides in open communication with adjacent bores continuously from the upper to the lower surface of the implant; and
  a plurality of bone plugs sized to fit into each of said cylindrical internal bores.

18. The kit as set forth in claim 17 wherein each implant internal cavity has three internal bores and a plug is provided for fitting into each bore.

19. The kit as set forth in claim 17 wherein the bone plug material is selected from the group consisting of allograft bone, autograft bone, bone morphogenic proteins, bioceramics and hydroxyapatite.

20. The kit as set forth in claim 19 wherein each of said plurality of implant bodies includes a slit in the sidewall in communication with said generally cylindrical bores.

21. An apparatus for facilitating fusion of adjacent vertebrae, comprising:
  an implant body dimensioned for positioning within an intervertebral space between upper and lower vertebrae to maintain the vertebrae in desired space relation to facilitate fusion thereof, said implant body including lower and upper surfaces for engaging the respective lower and upper vertebrae, and first and second side wall portions extending between said upper and lower surfaces, said first and second side wall portions being substantially solid wherein said body has an internal cavity formed by three bores extending between the upper and lower surface, said bores having sidewalls in open communication with adjacent bores.

22. The apparatus as set forth in claim 21 wherein said first and second sidewalls have a longitudinal slit in communication with each of said bores.

23. The apparatus as set forth in claim 22 wherein said bores are generally cylindrical.

24. The apparatus as set forth in claim 1 wherein said implant includes three bores.

* * * * *